United States Patent [19]

Raml et al.

[11] Patent Number: 4,804,351

[45] Date of Patent: Feb. 14, 1989

[54] SURGICAL BRASSIERE

[76] Inventors: Nancy M. Raml, 21405 Sierra Dr.;
Connie J. Janiszewski, 21415 Sierra
Dr., both of Waukesha, Wis. 53186

[21] Appl. No.: 120,862

[22] Filed: Nov. 16, 1987

[51] Int. Cl.4 ............................................... A41C 3/02
[52] U.S. Cl. ....................................... 450/58; 450/71;
2/DIG. 1
[58] Field of Search ....................... 450/58, 59, 71, 82,
450/83, 36; 2/DIG. 1

[56] References Cited

U.S. PATENT DOCUMENTS

| | | | |
|---|---|---|---|
| 1,956,250 | 4/1934 | Rosenthal | 128/280 |
| 2,386,530 | 10/1945 | Witkower | 2/42 |
| 2,492,303 | 12/1949 | Lo Cascio | 2/42 |
| 2,662,522 | 12/1953 | Muller | 450/58 X |
| 2,676,321 | 4/1954 | Dubner | 450/83 X |
| 2,678,446 | 5/1954 | Fellner | 450/82 X |
| 3,112,750 | 12/1963 | Jonas | 128/510 |
| 3,229,694 | 1/1966 | Koropp | 128/510 |
| 3,439,682 | 4/1969 | DeFru | 128/460 |
| 3,478,747 | 11/1969 | Sachs | 450/59 |
| 3,814,107 | 6/1974 | Greenblatt et al. | 128/480 |

Primary Examiner—Werner H. Schroeder
Assistant Examiner—Jeanette E. Chapman
Attorney, Agent, or Firm—Michael, Best & Friedrich

[57] ABSTRACT

A surgical brassiere for reducing stress along a mid-sternal incisional line of a female patient following cardiothoracic surgery includes a pair of bust support cups positioned over the breasts of the patient so as to form an exposed gap over the area of the patient's sternum. A ventilated panel is secured over the gap to provide protection to the mid-sternal incision and can be unsecured as required for purposes of routine examination or nursing care. A pair of inner straps, detachably secured across the gap between the bust support cups, assure that support continues to be provided while the ventilated panel is thus unsecured. To increase patient comfort, the brassiere further includes relatively wide, padded shoulder straps, and a flexible backstrap assembly, including a pair of criss-crossed flexible elastic straps provides additional support to further promote post-operative recovery.

12 Claims, 1 Drawing Sheet

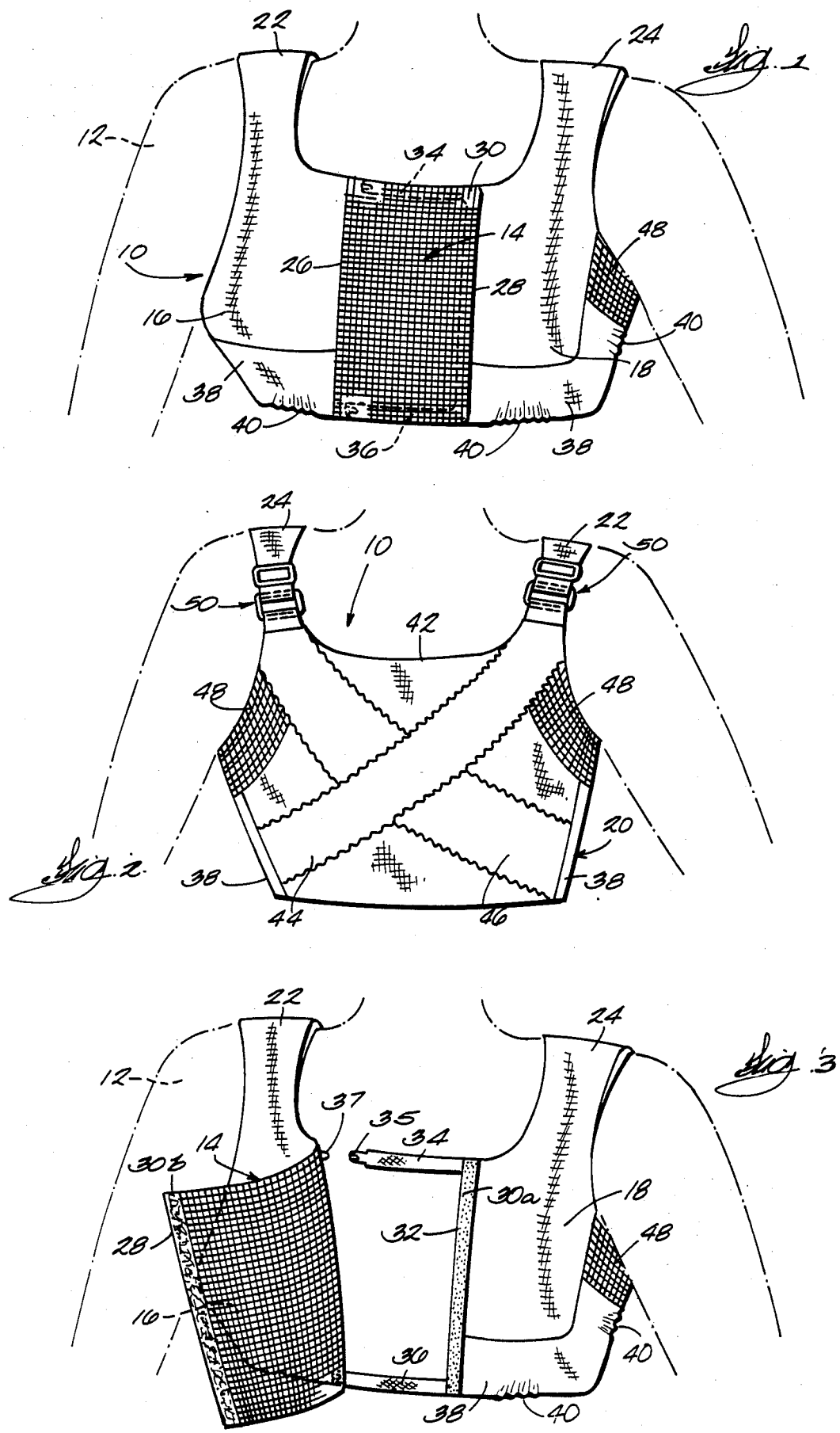

SURGICAL BRASSIERE

BACKGROUND OF THE INVENTION

This invention relates generally to brassieres and, more particularly, to brassieres suitable for use by female patients following cardio-thoracic surgery.

Cardio-thoracic surgical procedures typically include an incision extending from the suprasternal notch to the zyphoid process. Following surgery, the incision is typically closed by means of external staples or subcutaneous silk sutures. In the case of female patients, considerable stress can be placed on the incisional line by reason of the weight of the breasts. As such stress can be greatest when the female patient is reclining, post-operative orders frequently call for female cardio-thoracic surgery patients to wear a brassiere twenty-four hours a day. Typically, such patients have provided and worn their own, conventional brassieres in complying with such post-operative orders.

For a number of reasons, conventional brassieres are not entirely appropriate for use by bedridden, semi-ambulatory female patients following cardio-thoracic surgery. In particular, conventional brassieres do not provide adequate ventilation of the incisional wound nor do such brassieres allow access to the incision for routine examination or nursing care except through removal of the brassiere. Furthermore, such conventional brassieres typically lack adequate back support to provide meaningful assistance to the patient during coughing and deep breathing or while moving into and out of bed. Finally, as conventional brassieres can be particularly uncomfortable following cardio-thoracic surgery, patients sometimes fail to comply with the requirement that a brassiere be worn twenty-four hours a day following surgery.

Because of their various inadequacies, conventional brassieres can give rise to a variety of undesirable complications when utilized during post-operative care. For example, inadequate ventilation can interfere with cooling and drying and can, thus, give rise to infection of the incisional line. Similarly, poor or inadequate support can interfere with rapid healing and recovery as can the tendency of conventional brassieres to interfere with coughing or deep breathing. Finally, non-compliance with post-operative orders, stemming from discomfort associated with the use of conventional brassieres, can further interfere with rapid and effective healing and can, thus, significantly lengthen the post-operative recovery.

In view of the foregoing, it is a general object of the present invention to provide a new and improved brassiere.

It is a further object of the present invention to provide a new and improved brassiere which is particularly well adapted for use by female patients following cardio-thoracic surgery.

It is a still more specific object of the present invention to provide a new and improved brassiere which provides ventilation of a mid-sternal incisional line as well as access to the incisional line for purposes of routine examination or nursing care.

It is a still more specific object of the present invention to provide a new and improved brassiere which provides adequate and effective support during post-operative care and which maximizes patient compliance with post-operative orders by minimizing patient discomfort during use.

SUMMARY OF THE INVENTION

The invention is directed to a brassiere adapted to encircle the torso of a wearer so as to support the wearer's breasts, the brassiere including a ventilated panel located so as to overlie the area of the wearer's sternum when the brassiere is worn by the wearer.

The invention is also directed to a brassiere adapted to encircle the torso of a wearer so as to support the wearer's breasts. The brassiere includes an openable ventilated panel adapted to provide access to the area of the wearer's sternum, and further includes means for maintaining support of the wearer's breasts when the ventilated panel is open so that access to the area of the wearer's sternum can be obtained without destroying the support provided to the wearer's breasts by the brassiere.

The invention is also directed to a brassiere comprising a first bust support cup, a second bust support cup, first means for supporting the first bust support cup over one breast of a wearer and for supporting the second bust support cup over the other breast of the wearer so as to form an open gap between the first and second bust cups over the area of the wearer's sternum. The brassiere further includes a ventilated panel adapted to be selectively secured and unsecured between the first and second bust support cups and over the gap when the first and second bust support cups are positioned over the breasts of the wearer. The brassiere further includes second means interconnecting the first and second bust support cups across the gap for maintaining the first and second bust support cups in position over the breasts of the wearer when the ventilated panel is unsecured from between the first and second bust support cups.

A principal feature of the present invention is the provision of a brassiere, suitable for use following cardio-thoracic surgery, wherein access to a mid-sternal incisional line can be obtained without removing the brassiere or otherwise relieving the support provided by the brassiere.

Another principal feature of the invention is the provision of a brassiere having an open weave or ventilated panel positioned so as to provide ventilation in the area of the wearer's sternum when the brassiere is being worn.

Still another principal feature of the present invention is the provision of a brassiere, suitable for use by female patients following cardio-thoracic surgery, wherein relatively wide shoulder straps, and a criss-cross construction of elastic back panels are provided to improve comfort and increase the back support provided by the brassiere during use.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a front perspective view of a surgical brassiere constructed in accordance with the invention showing a front ventilated panel in a closed position.

FIG. 2 is a rear perspective view of the surgical brassiere shown in FIG. 1.

FIG. 3 is a front perspective view, similar to FIG. 1, showing the ventilated panel in an open position.

DESCRIPTION OF THE PREFERRED EMBODIMENT

Referring to the drawings, a surgical brassiere 10 constructed in accordance with the invention comprises a flexible garment adapted to encircle the torso of a wearer 12 so as to support the wearer's breasts. In accordance with one principal feature of the invention, the brassiere 10 includes an openable ventilated panel 14 adapted to provide access to the area of the wearer's sternum. Preferably, the openable front panel 14 is made of stretchable open weave fabric having a cross pattern as illustrated. Alternatively, the front panel 14 can comprise an open weave stretch lace to provide improved aesthetic qualities in combination with improved ventilation.

The brassiere 10 further comprises first and second bust support cups 16 and 18 which are dimensioned to overlie the right and left breasts, respectively, of the wearer 12. In addition, means are provided for supporting the first and second bust support cups 16 and 18 over the breasts of the wearer 12 so as to form an open gap between the first and second bust support cups 16 and 18 over the area of the sternum. In the embodiment illustrated, such means take the form of a flexible back strap assembly 20 adapted to extend across the back of the wearer 12 at substantially the level of the wearer's breasts, in combination with first and second shoulder straps 22 and 24, coupled to the flexible back strap assembly 20, adapted to extend over the wearer's right and left shoulders toward the wearer's right and left breasts.

When worn by a patient following cardio-thoracic surgery, the ventilated panel 14, as illustrated in FIG. 1, is positioned over the wearer's sternum and thus provides ventilation of the post-operative incision, which typically extends from the suprasternal notch to the zyphoid process. Accordingly, the ventilated panel 14 helps to promote cooling and drying of the incisional line to help promote healing.

As further illustrated in FIG. 1, the ventilated panel 14 is substantially rectangular in form and includes one edge 26 which is firmly joined to the first bust support cup 16 by means of stitching or other fastening. The opposite edge 28 of the ventilated panel 14 extends over the gap formed between the first and second bust support cups 16 and 18 and is releasably secured to the second bust support cup 18 by means of a releasable fastening. Preferably, the releasable fastening for releasably securing the opposite edge 28 of the ventilated panel 14 to the second bust support cup 18 comprises a synthetic hook and loop fastener 30 such as Velcro. As best seen in FIG. 3, one strip 30a of the hook and loop fastener extends along the entire length of the inner edge 32 of the second bust support cup while a continuous strip 30b of the mating hook and loop fastener is fastened along the outer vertical edge 28 of the ventilated panel 14. By pressing the outer edge 28 of the ventilated panel 14 downwardly onto the inner edge 32 of the second bust support cup 18, the ventilated panel 14 can be retained in the closed position shown in FIG. 1.

In order to permit the ventilated panel 14 to be opened for purposes of routine examination or nursing care, additional means, interconnecting the first and second bust support cups 16 and 18 across the gap formed therebetween, are provided for maintaining the first and second bust support cups 16 and 18 in position over the breasts of the wearer 12 when the ventilated panel 14 is unsecured from between the first and second bust support cups 16 and 18. In the illustrated embodiment, such means includes a pair of upper and lower transverse inside straps 34 and 36 which are adapted to extend between the first and second bust support cups across the area of the incision.

As best seen in FIG. 3, the upper and lower inside straps 34 and 36 are each relatively narrow and are firmly attached, at one end, to the inner edge 32 of the second bust support cups 18. Each of the upper and lower inner straps 34 and 36 terminates under the inner edge 26 of the first bust support cup 16, and means are provided for removably securing the outermost ends of the upper and lower inside straps 34 and 36 to the first bust support cup. In the illustrated embodiment, such means includes single metallic hooks 35 fastened to each of the outermost ends of the upper and lower inside straps 34 and 36, and further includes corresponding metallic loops 37 fastened to the undersurface of the first bust support cup 16 adjacent the upper and lower ends of the inner edge 26 thereof. Alternatively, synthetic hook and loop fasteners, such as Velcro, can be provided for detachably securing the upper and lower inside straps 34 and 36 to the first bust support cup 16. Once the upper and lower inside straps 34 and 36 are attached to the first bust support cup 16 across the incisional line, the ventilated panel 14 can be opened and closed as desired without destroying the support provided by the brassiere 10 or increasing the stress placed on the incisional line. The use of upper and lower inside straps 34 and 36 provides substantially equal distribution of pressure when the garment is worn and thereby further avoids the development of undue stress along the incisional line.

Preferably, the upper portion of each bust support cup 16 and 18, together with the front portion of each shoulder strap 22 and 24, is constructed of a poly-cotton weave fabric having elasticity. In addition, each of the bust support cups 16 and 18 is provided with an absorbent panel 88 extending underneath each breast and along the wearer's side. In order to provide comfortable and effective support, each absorbent panel is preferably made of one-eighth or one-quarter inch covered quilted fiber-fill sewn with elastic thread or the like. Preferably, a plurality of elastic easements 40, each comprising a region of additional elasticity, are formed in the undersurface of each absorbent panel 38 beneath each breast and under the wearer's arms in order to permit a chest tube (not shown) to be run under the brassiere without undue stretching or discomfort.

To further improve comfort during periods of extended wear, the shoulder straps 22 and 24 are relatively wider than are the shoulder straps of conventional brassieres and are padded for extra comfort. In addition, the back strap assembly 20 of the surgical brassiere 10 includes, as best seen in FIG. 2, an elastic panel 42 having a pair of flexible elastic straps 44 and 46 extending across the wearer's back as shown in order to provide firm back support. Preferably, each of the criss-crossed flexible elastic straps 44 and 46 is formed of Spandex or similar material.

Additional side support is provided by means of the absorbent panels 38 which extend around the sides of the wearer's torso, and by additional ventilated panels 48 extending along the underarms on each side of the garment. Preferably, the width of the garment along the sides of the wearer's torso is relatively great so that the main concentration of support is to the side of the breast. Such support is preferable when the female patient is in a reclining position for long periods of time following surgery.

To help improve the fit and thereby enhance the wearer's comfort, each of the shoulder straps 22 and 24 includes a length adjustment feature 50, of known construction, as best seen in FIG. 2.

The surgical brassiere 10 as described herein functions to maintain ample support of a female patient's breasts so as to avoid undue stress on the incisional line following cardio-thoracic surgery. In particular, the surgical brassiere 10 provides support which is directed along the side of each breast so as to avoid stress along the incisional line. In addition, the ventilated panel 14, in combination with the upper and lower inside straps 34 and 36, permits access to the incisional line, when desired, without simultaneously reducing the support provided by the garment. The criss-crossed back straps 44 and 46 provide considerable back support to further improve comfort and help avoid the development of stress along the incisional line, while the relatively wide, padded shoulder straps 22 and 24 further contribute to comfort during periods of extended wear. Finally, the improved ventilation provided by the ventilated panel 14 greatly improves oxygenation of the incision and helps promote fast healing while reducing the risk of infection.

While a particular embodiment of the invention has been shown and described, it will be obvious to those skilled in the art the changes and modifications may be made therein without departing from the invention in its broader aspects, and, therefore, the aim in the appended claims is to cover all such changes and modifications as fall within the true spirit and scope of the invention.

We claim:

1. A brassiere adapted to encircle the torso of a wearer so as to support the wearer's breasts, said brassiere including a ventilated panel located so as to overlie the area of the wearer's sternum when said brassiere is worn by the wearer, and said ventilated panel can be opened so as to gain access to the area of the wearer's sternum.

2. A brassiere in accordance with claim 1 further including means for maintaining support of the wearer's breasts when said ventilated panel is open so that access to the area of the wearer's sternum can be obtained without thereby destroying the support provided to the wearer's breasts by said brassiere.

3. A brassiere in accordance with claim 2 wherein said ventilated panel is formed of an open weave fabric so as to provide ventilation to the area of the wearer's sternum.

4. A brassiere adapted to encircle the torso of a wearer so as to support the wearer's breasts, said brassiere including an openable panel adapted to provide access to the area of the wearer's sternum, and further including means for maintaining support of the wearer's breasts when said panel is open so that access to the area of the wearer's sternum can be obtained without thereby destroying the support provided to the wearer's breasts by said brassiere.

5. A brassiere in accordance with claim 4 wherein said brassiere further includes first and second bust support cups separated by an open gap when said brassiere is worn by a wearer and wherein said means for maintaining support comprises an elongate strap adapted to extend across said gap and interconnect said first and second bust support cups.

6. A brassiere in accordance with claim 5 wherein said means for maintaining support includes a pair of said straps extending across said gap so as to define a substantially open area over the wearer's sternum and under said openable panel.

7. A brassiere comprising:
a first bust support cup;
a second bust support cup;
first means for supporting said first bust support cup over one breast of a wearer and for supporting said second bust support cup over the other breast of the wearer so as to form an open gap between said first and second bust support cups over the area of the sternum of the wearer;
a ventilated panel adapted to be selectively secured and unsecured between said first and second bust support cups and over said gap when said first and second bust support cups are positioned over the breasts of the wearer; and
second means interconnecting said first and second bust support cups across said gap for maintaining said first and second bust support cups in position over the breasts of the wearer when said ventilated panel is unsecured from between said first and second bust support cups.

8. A brassiere in accordance with claim 7 wherein said second means includes an elongate strap adapted to extend across said gap between said first and second bust support cups.

9. A brassiere in accordance with claim 8 wherein said strap includes one end substantially permanently fastened to one of said first and second bust support cups and another end adapted to be detachably secured to the other of said first and second bust support cups.

10. A brassiere in accordance with claim 9 wherein said brassiere includes a pair of said straps.

11. A brassiere in accordance with claim 7 wherein said ventilated panel is selectively secured and unsecured by means of a synthetic hook and loop fastener.

12. A brassiere for providing support to a wearer's breasts following cardio-thoracic surgery so as to avoid stress in the area of an incision formed substantially along a line extending from the suprasternal notch to the zyphoid process, said brassiere comprising:
a flexible backstrap assembly adapted to extend across the back of the wearer at substantially the level of the wearer's breasts;
a first shoulder strap coupled to said flexible backstrap assembly and adapted to extend over one shoulder of the wearer toward the adjacent one of the wearer's breasts;
a second shoulder strap coupled to said flexible backstrap assembly and adapted to extend over the wearer's other shoulder toward the wearer's other breast;
a first bust support cup coupled to one end of said flexible backstrap assembly and to one end of said first shoulder strap and dimensioned to overlie the adjacent one of the wearer's breasts except in the area of the incision;
a second bust support cup coupled to the other end of said flexible backstrap assembly and to one end of said second shoulder strap and dimensioned to overlie the other one of the wearer's breasts except in the area of the incision;

first and second inside straps adapted to extend between said first and second bust support cups across the incision, said first and second inside straps being dimensioned and located to form an open area bounded by said first and second inside straps and said first and second bust support cups over the incision when said brassiere is being worn by the wearer;

a ventilated panel dimensioned to overlie said open area; and means for removably securing said ventilated panel over said open area so as to selectively provide access to the incision when desired without requiring removal of said brassiere and so as to provide protection to the incision when said access is not desired while maintaining ventilation of the incision.

* * * * *